US012349677B2

(12) United States Patent
Agarkhed et al.

(10) Patent No.: US 12,349,677 B2
(45) Date of Patent: Jul. 8, 2025

(54) ANTIMICROBIAL COMPOSITION

(71) Applicant: CONOPCO, INC., Trumbull, CT (US)

(72) Inventors: Ajit Manohar Agarkhed, Thane (IN);
Khushbu Agarwal, Bangalore (IN);
Amitabha Majumdar, Bangalore (IN);
Mruthyunjaya Swamy Mathapathi,
Bangalore (IN)

(73) Assignee: Conopco, Inc., Hoboken, NJ (US)

( * ) Notice: Subject to any disclaimer, the term of this patent is extended or adjusted under 35 U.S.C. 154(b) by 350 days.

(21) Appl. No.: 17/281,611

(22) PCT Filed: Oct. 28, 2019

(86) PCT No.: PCT/EP2019/079347
§ 371 (c)(1),
(2) Date: Mar. 31, 2021

(87) PCT Pub. No.: WO2020/089145
PCT Pub. Date: May 7, 2020

(65) Prior Publication Data
US 2021/0392884 A1 Dec. 23, 2021

(30) Foreign Application Priority Data

Oct. 31, 2018 (EP) ..................... 18203709

(51) Int. Cl.
| | | |
|---|---|---|
| *A01N 33/08* | (2006.01) | |
| *A01N 31/08* | (2006.01) | |
| *A01N 31/16* | (2006.01) | |
| *A61K 8/34* | (2006.01) | |
| *A61K 8/41* | (2006.01) | |
| *A61Q 17/00* | (2006.01) | |
| *A61Q 19/10* | (2006.01) | |

(52) U.S. Cl.
CPC ............. *A01N 33/08* (2013.01); *A01N 31/08* (2013.01); *A01N 31/16* (2013.01); *A61K 8/34* (2013.01); *A61K 8/347* (2013.01); *A61K 8/41* (2013.01); *A61Q 17/005* (2013.01); *A61Q 19/10* (2013.01)

(58) Field of Classification Search
CPC ........ A01N 31/08; A01N 33/08; A61K 8/347; A61K 8/41; A61Q 17/005; A61Q 19/10
See application file for complete search history.

(56) References Cited

U.S. PATENT DOCUMENTS

| | | | |
|---|---|---|---|
| 5,614,538 A | 3/1997 | Nelson, Jr. | |
| 7,537,752 B2 | 5/2009 | De Lacharriere et al. | |
| 7,723,279 B2 | 5/2010 | Lestage et al. | |
| 9,132,103 B2 | 9/2015 | Medepalli et al. | |
| 2005/0233930 A1 | 10/2005 | Cheung et al. | |
| 2006/0047005 A1* | 3/2006 | Salamone | A61L 12/143 |
| | | | 514/642 |
| 2006/0067958 A1 | 3/2006 | Valencia et al. | |
| 2009/0143714 A1 | 6/2009 | Millikin et al. | |
| 2011/0223114 A1 | 9/2011 | Chakrabortty et al. | |
| 2012/0276022 A1 | 11/2012 | Medepalli et al. | |
| 2013/0274345 A1 | 10/2013 | Hurtmanns et al. | |
| 2014/0311515 A1 | 10/2014 | Barne et al. | |
| 2014/0315875 A1 | 10/2014 | Jiang et al. | |
| 2014/0343155 A1 | 11/2014 | Jayaraman et al. | |
| 2016/0324754 A1 | 11/2016 | Cure | |
| 2018/0338494 A1 | 11/2018 | Agarkhed et al. | |
| 2019/0264146 A1 | 8/2019 | Agarkhed et al. | |

FOREIGN PATENT DOCUMENTS

| | | |
|---|---|---|
| CN | 1168653 | 12/1997 |
| CN | 102186341 | 9/2011 |
| CN | 102510723 | 6/2012 |
| CN | 103890160 | 6/2014 |
| CN | 103998011 | 8/2014 |
| CN | 104066418 | 9/2014 |
| CN | 104353419 | 2/2015 |
| DE | 202007002978 | 5/2007 |
| EP | 1875895 | 1/2008 |
| JP | 2002187814 | 7/2002 |
| KR | 20160057248 | 6/2016 |
| WO | WO9850005 | 11/1998 |
| WO | WO9855080 | 12/1998 |
| WO | WO9855099 | 12/1998 |
| WO | WO0047184 | 8/2000 |
| WO | WO03075883 | 9/2003 |
| WO | WO2004006876 | 1/2004 |
| WO | WO2004035723 | 4/2004 |
| WO | WO2006026170 | 3/2006 |
| WO | WO2008021441 | 2/2008 |
| WO | WO08085446 | 7/2008 |

(Continued)

OTHER PUBLICATIONS

Bertin et al., "Clinical evidence for the activity of tetrahydroxypropyl ethylenediamine (THPE), a new anti-aging active cosmetic", J. Drugs Derm., Oct. 1, 2011, 10(10), pp. 1102-1105 (abstract) (Year: 2011).*
Occupational Safety and Health Administration, "Biological Agents—Overview", accessed Aug. 21, 2024 at https://osha.gov/biological-agents (Year: 2024).*
Search Report & Written Opinion in EP15196697; Feb. 16, 2016; European Patent Office (EPO).
Milind S. Shintre et al.; Efficacy of an alcohol-based healthcare hand rub containing synergistic combination of farnesol and benzethonium chloride; International Journal of Hygiene and Environmental Health; 2006; pp. 477-487; XP028043393; vol. 209, No. 5; Elsevier.

(Continued)

*Primary Examiner* — Dominic Lazaro
(74) *Attorney, Agent, or Firm* — Krista J. Aiello

(57) ABSTRACT

This invention relates to an antimicrobial composition, more particularly a personal care composition like a soap bar. It more particularly relates to a composition comprising an essential oil compound and a tetra hydroxy alkylene amine compound which interact synergistically to provide the desired result.

13 Claims, No Drawings

(56) References Cited

FOREIGN PATENT DOCUMENTS

| WO | WO2010046238 | 4/2010 |
|----|--------------|--------|
| WO | WO2011036048 | 3/2011 |
| WO | WO2011151171 | 12/2011 |
| WO | WO2013064315 | 5/2013 |
| WO | WO2017108445 | 6/2017 |

OTHER PUBLICATIONS

Search Report & Written Opinion in EP15196704; May 20, 2016; European Patent Office (EPO).
Database WPI Week 201530; 2015; pp. 1-3; XP002756571.
GNPD Mintel; Anti-dandruff Shampoo; Laboratoires Klorane Thym Rouge d'Espagne (Red Thyme from Spain) Shampoo Antipelliculaire; 2010; pp. 1-4; XP002756570; Record ID 1268029; Belgium.
Search Report and Written Opinion in PCTEP2016076820; Jan. 30, 2017; World Intellectual Property Org. (WIPO).
Search Report and Written Opinion in PCTEP2016076842; Dec. 15, 2016; World Intellectual Property Org. (WIPO).
Hcini et al.; Chemical Composition of the Essential Oil of Rosemary (*Rosmarinus officinalis* L.) of Tunisin Origin; Asian Journal of Chemistry; 2013; pp. 2601-2603 (also as XP55533760); vol. 25, No. 5.
GNPD Mintel; Dr.Ci:Labo; Orange & Eucalyptus Herbal Hand Gel; May 2018; pp. 1-3, XP55533534, Record ID 5520271; Japan.
GNPD Mintel; Cleansing Soap-EX; Dr.Ci:Labo; May 2017; pp. 1-4, XP55533699, Record ID 4835789; Japan.
Search Report and Written Opinion in EP18203709; Jan. 14, 2019; European Patent Office (EPO).
GNPD Mintel; Antiseptic Moisturising Gel; Needs Gel Antisséptico Hidratante; Nov. 2014; pp. 1-3 Record ID 2767103; Brazil.
GNPD Mintel; Cleansing Foam; It's Skin Prestige Jeju Wild Ginseng; Sep. 2017; pp. 1-3 Record ID 5084765; South Korea.
GNPD Mintel; Deodorizing Foot Spray; Freeman Bare Foot Repair!; Jul. 2017; pp. 1-3 Record ID 4945675; South Korea.
GNPD Mintel; Lavender with Chamomile Fragrance Antiseptic Moisturising Gel; Needs Gel Antisséptico Hidratante Lavanda com Camomila; Jun. 2016; pp. 1-3; Record ID 4078395; Brazil.
Search Report and Written Opinion in PCTEP2019079347; Jan. 17, 2020; World Intellectual Property Org. (WIPO).
IPRP in PCTEP2016076820; May 28, 2018; World Intellectual Property Org. (WIPO).
IPRP in PCTEP2016076842; May 29, 2018; World Intellectual Property Org. (WIPO).
Wang, Shengshou; New Clinical Pharmacology and Drug Application; Jilin Science and Technology Press; Mar. 2019; pp. 37, with english translation.
GNPD Database (Online) Mintel; Hand Sanitizer; LCN Spa Goa; Sep. 2012; pp. 1-7, Record ID 1855230; Germany.
Derwich et al.; GC/MS analysis of volatile constituents and antibacterial activity of the essential oil of the leaves of Eucalyptus globulus in atlas median from Morocco; Advances in Natural and Applied Sciences; Sep. 2009; pp. 1-14; vol. 3, Issue 3; American-Eurasian Network for Scientific Information.
Jabalpurwala et al.; A comparison of citrus blossom volatiles; Phytochemistry; Sep. 2009; pp. 1428-1434; vol. 70; Elsevier Ltd.
Bonnlander et al.; Analysis of enantiomeric linalool ratio in green and roasted coffee; Flavour and Fragrance Journal; Mar. 2006; pp. 637-641; vol. 21; John Wiley & Sons Ltd.
Lee at al.; Analysis of volatile components isolated from Hawaiian green coffee beans (*Coffea arabica* L.); Flavour and Fragrance Journal; 2002; pp. 349-351; vol. 17; Wiley InterScience.
GNPD Database (Online) Mintel; Beauty Creator Anti-Ageing Cleansing Milk; Soroya; Dec. 2004; pp. 1-3 Record ID 324729.
How to display all ingredients of cosmetics, etc.; Notification No. 163 issued by Pharmaceutical Affairs Bureau/Notification No. 220 by Compliance and Narcotics Division; Mar. 6, 2001; pp. 1-4, with English translation; https://www.japal.org./dom/notice/000833.html; Director of the Pharmaceutical Pharmacy Examination/Management Division, Ministry of Health, Labor and Welfare/Director of the Pharmaceutical Pharmacy Monitoring and Guidance and Narcotics Countermeasures Division, Ministry of Health, Labor and Welfare; Japan.

\* cited by examiner

ANTIMICROBIAL COMPOSITION

CROSS REFERENCE TO RELATED APPLICATIONS

The present application is a U.S. National Phase Application under 35 U.S.C. § 371 of International Application No. PCT/EP2019/079347, filed on Oct. 28, 2019, which claims priority to European Patent Application No. 18203709.3, filed on Oct. 31, 2018, the contents of which are incorporated herein in their entireties.

FIELD OF THE INVENTION

This invention relates to an antimicrobial composition. The invention more particularly relates to a personal care composition e.g that for care of hair, body, hand or face which provides anti-microbial efficacy. It more particularly relates to a cleansing composition comprising actives that interact to provide synergistic antimicrobial efficacy and also for giving protection against germs in between two washes.

BACKGROUND OF THE INVENTION

The invention relates to an anti-microbial composition useful for cleaning of any body part but especially suitable for hand hygiene or for body or facial cleansing.

Handwashing with antimicrobial soaps, especially after use of the toilet and/or before partaking of food has been identified as one of the most effective ways of improving human mortality, morbidity and for improving the general quality of life. Sanitizing and disinfecting soap compositions comprising chlorine-based antimicrobial agent such as triclosan are known. If the user, uses a soap where the antimicrobial activity is low or slow, he is likely to have skin with relatively inadequate bacterial removal and may cause contamination of further animate and/or inanimate surfaces and lead to spreading of pathogens and consequent diseases. Hence providing hand and body wash compositions with enhanced antimicrobial activity is paramount for providing enhanced health and quality of life of consumers.

While the above mentioned problems are mitigated to a large extent through use of compositions containing known antimicrobial actives, there is a need for ensuring enhanced antimicrobial efficacy while at the same time ensuring protection of the skin against germs in between two washes. The present inventors have found that this benefit can be obtained when certain essential oils are combined with select tetra hydroxy alkylene amine compounds.

WO06026170 (Bausch & Lomb) discloses a composition comprising: an effective disinfecting amount of one or more antimicrobial agents and one or more (hydroxyalkyl)diamine-based buffers, (hydroxyalkoxy)diamine-based buffers or a combination thereof.

To our knowledge, the essential oil compounds claimed in the present invention in combination with the selected tetra hydroxy alkylene amine compounds have not been disclosed for highly efficient antibacterial action while also providing protection of the skin against bacteria which may attack the skin between two cleansing operations.

It is thus an object of the present invention to provide for an antimicrobial composition that exhibits enhanced antimicrobial activity long after the skin has been washed with this composition.

It is another object of the present invention to provide for an antimicrobial composition that is effective when used in a personal cleansing composition especially one comprising soap.

It is yet another object of the present invention to provide for an antimicrobial composition that is effective against invading bacteria long after the skin has been washed with the composition.

SUMMARY OF THE INVENTION

According to the first aspect of the present invention there is an antimicrobial composition comprising
(i) a compound of the general formula 1

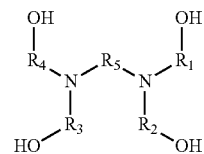

Where R1 to R4 are each independently a linear or branched carbon chain having 2 to 5 carbon atoms; and R5 is a carbon chain having 1 to 4 carbon atoms; and
(ii) an essential oil compound of general formula 2 having the structure

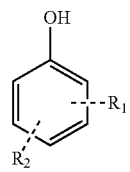

Where R1 is H, OH or OR where R is alkyl chain with 1 to 5 carbon atoms;
R2 is a C1 to C6 linear alkyl group; or C3 to C6 branched alkyl group; or C5 to C6 cyclic or heterocyclic alkyl group; or a C6 aromatic group.

The second aspect of the present invention relates to a method of providing antimicrobial efficacy to skin comprising the step of applying a composition of the first aspect on to the desired skin surface followed by wiping the composition off the surface or rising the surface with water to be substantially free of said composition.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. In other words, in specifying any ranges of values, any particular upper value can be associated with any particular lower value.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

By 'an antimicrobial composition' as used herein, is meant to include a composition for topical application to skin, hair and/or scalp of mammals, especially humans. Such a composition is generally applied on to the desired topical surface of the body for a period of time from a few seconds to up to several minutes. When the period of time of application is low say of the order of a few seconds to a few minutes after which the composition is rinsed off with water or wiped away, such a composition is known as a cleansing composition or a wash-off composition. When the composition is applied for longer period of time say from several minutes to up to 24 hours and washed off usually during the process of normal personal cleaning, such a composition is known as a leave-on composition. The composition as per the present invention may be of the wash-off or of the leave-on type. Of the two, it is preferably of the wash-off type. It includes any product applied to a human body for also improving appearance, cleansing, odor control or general aesthetics. The composition of the present invention can be in the form of a liquid, lotion, cream, foam, scrub, gel, bar, shampoo, conditioner, handwash, facewash or bodywash product. It is more preferably used for disinfecting the hand or other parts of the human body.

The present invention more particularly relates to an antimicrobial cleansing composition.

The antimicrobial composition of the invention includes a compound of the general formula 1:

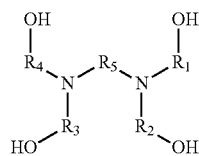

Where R1 to R4 are each independently a linear or branched carbon chain having 2 to 5 carbon atoms; and R5 is a carbon chain having 1 to 4 carbon atoms.

It is preferred that R1 to R4 are carbon chains with 3 or 4 carbon atoms, more preferably carbon chains with 3 carbon atoms. It is preferred that R5 is a carbon chain having 2 or 3 carbon atoms, more preferably a carbon chain with two carbon atoms. Further more preferably, R5 is a linear carbon chain.

The most preferred compound of formula 1 is tetrahydroxypropyl ethylenediamine (THPE) which has the formula

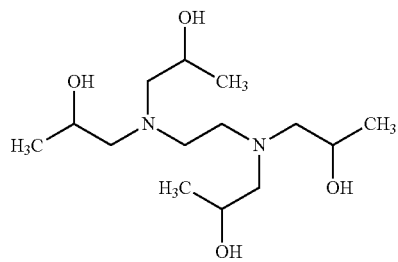 [SMILES: CC(O)CN(CCN(CC(C)O)CC(C)O)CC(C)O]

Compound of formula 1 is preferably included in 0.1 to 10%, more preferably 0.1 to 5%, further more preferably 0.2 to 3% by weight of the composition.

The composition of the invention includes an essential oil compound of general formula 2 having the structure

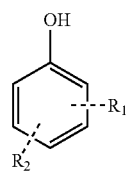

Where R1 is H, OH or OR where R is an alkyl chain with 1 to 5 carbon atoms; R2 is a C1 to C6 linear alkyl group; or C3 to C6 branched alkyl group; or C5 to C6 cyclic or heterocyclic alkyl group; or a C6 aromatic group.

The most preferred essential oil compounds as per compound of formula 2 for use in the composition of the invention are selected from thymol, carvacol, (E)-2(prop-1-enyl) phenol, 2-propylphenol, 4-pentylphenol, 4-sec-butylphenol, 2-benzyl phenol, or eugenol or combinations thereof.

The structure of these compounds are given below:

The structure of thymol is given below:

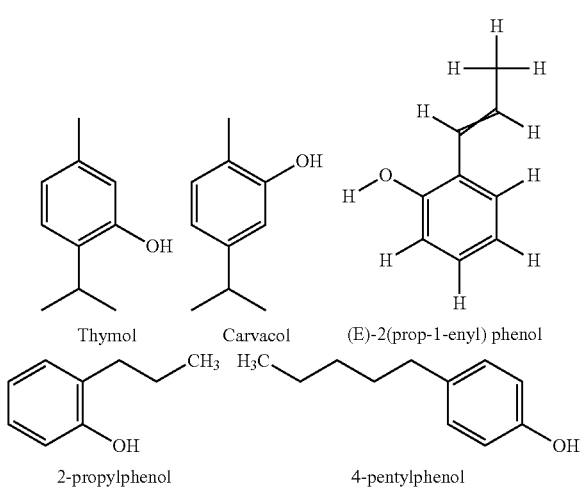

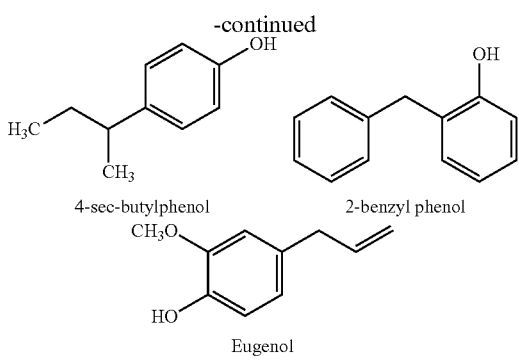

4-sec-butylphenol     2-benzyl phenol

Eugenol

Of the above essential oil compounds, thymol, carvacrol or eugenol. are more preferred for use in the composition of the invention.

The essential oil compounds are preferably included in 0.001 to 1%, preferably 0.005 to 1%, further more preferably 0.005 to 0.5% by weight of the composition.

It is further more preferred that an additional essential oil compound of the terpene group is included in the composition of the invention. The most preferred compound of the terpene group is terpineol. The terpineol is preferably selected from alpha-terpineol, beta-terpineol, gamma-terpineol or mixtures thereof. It is particularly preferred that the terpineol is alpha-terpineol. Terpineol may be added to the antimicrobial composition in purified form.

The structure of a terpineol compound is given below:

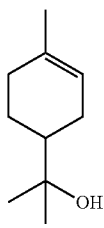

The antimicrobial composition preferably comprises 0.01 to 1% of terpineol more preferably from 0.05 to 0.5%, by weight of the composition.

As per an especially preferred aspect of the invention, the composition comprises a mixture of thymol and terpineol.

Without wishing to be bound by theory, the inventors believe that the anti-microbial efficacy is obtained long after the washing step is completed as a result of deposition of the active molecules on skin. These molecules then interact with the antimicrobial peptides already present on skin to deliver the desired benefit, between two washes.

In the present invention, antimicrobial alcohols (low molecular weight alcohols having one to 7 carbon atoms) are substantially absent. By substantially absent is meant that the concentration of the alcohol is less than an amount that is necessary for antimicrobial therapeutic activity. Preferably, the antimicrobial alcohol is present in less than 1%, more preferably less than 0.1% and optimally absent from the invention.

The composition of the invention preferably comprises a cosmetically acceptable base. According to one aspect, the cosmetically acceptable base comprises water. According to another preferred aspect, the base comprises a surfactant. Thus the cosmetically acceptable base comprises water, surfactant or combinations thereof. The cosmetically acceptable base may comprise an oil. An especially preferred aspect of the invention includes a cosmetically acceptable base which is an emulsion. In an emulsion, the oil and water are emulsified in the presence of an emulsifier (preferably a surfactant). It is preferred that the composition is prepared as a cream, lotion, gel, powder, ointment, body wash, hand wash or face wash product, shampoo, hair conditioner, or a soap composition preferably a soap bar. The product may be a body wash, a hand wash or a face wash product, most preferably a hand wash product.

The composition of the invention may be used for skin cleansing e.g. as a hand wash product. The antimicrobial composition may further comprise a surfactant. When surfactant is used, a particularly preferred surfactant is soap. Soap is a suitable surfactant for personal washing applications of the antimicrobial composition of the invention. The soap is preferably C8-C24 soap, more preferably C10-C20 soap and most preferably C12-C18 soap. The cation of the soap can be alkali metal, alkaline earth metal or ammonium. Preferably, the cation of the soap is selected from sodium, potassium or ammonium. More preferably the cation of the soap is sodium or potassium.

A typical fatty acid blend consisted of 5 to 30% coconut fatty acids and 70 to 95% fatty acids by weight of soap. Fatty acids derived from other suitable oils/fats such as groundnut, soybean, tallow, palm, palm kernel, etc. may also be used in other desired proportions.

When present, the soap, of the present is preferably present in an amount of 1 to 90%, preferably from 10 to 85%, more preferably 25 to 75% by weight of the composition.

Other preferred surfactants are nonionic surfactants, such as C8-C22, preferably C8-C16 fatty alcohol ethoxylates, comprising between 1 and 8 ethylene oxide groups when the product is in the liquid form. The surfactants are preferably selected from primary alkyl sulphate, secondary alkyl sulphonates, alkyl benzene sulphonates, or ethoxylated alkyl sulphates. The composition may further comprise an anionic surfactant, such as alkyl ether sulphate preferably those having between 1 and 3 ethylene oxide groups, either from natural or synthetic source and/or sulphonic acid. Especially preferred are sodium lauryl ether sulphates. Alkyl polyglucoside may also be present in the composition, preferably those having a carbon chain length between C6 and C16.

Preferred compositions may include other known ingredients such as perfumes, pigments, preservatives, emollients, sunscreens, emulsifiers, gelling agents and thickening agents. Choice of these ingredients will largely depend on the format of the composition.

Water is a preferred carrier. When water is present, it is preferably present in at least 1%, more preferably at least 2%, further more preferably at least 5% by weight of the composition. When water is the carrier, a preferred liquid composition comprises 10 to 99.8% by weight water. The liquid antimicrobial composition is useful as a skin antiseptic liquid, for skin cleansing, in particular for hand wash or a face wash. When water is the carrier, a preferred solid composition comprises 5 to 30% by weight water.

The solid antimicrobial composition is preferably in form of a shaped solid, more preferably a bar. The solid antimicrobial composition is particularly useful for skin cleansing in particular for hand wash or a face wash.

According to another aspect, inorganic particulate material is also a suitable carrier. When inorganic particulate material is the carrier, the antimicrobial composition is in a solid form. Preferably the inorganic particulate material is talc. When the inorganic particulate material is talc, the solid antimicrobial composition is particularly useful as a talcum powder for application on face or body.

In another aspect of the present invention, the composition of the present invention is suitable for use in wipes for personal hygiene.

The invention also relates to a method of providing antimicrobial efficacy to skin comprising the step of applying the composition of the invention on to the desired skin surface. The method is preferably non-therapeutic or cosmetic in nature.

This is followed by substantially removing the composition from the surface after a specified amount of time. Usually people spend about 10 seconds to 2 minutes washing their body parts and it is expected that in this time frame the desired antimicrobial action should have taken place. The time for washing is preferably from 10 second to one minute more preferably from 10 seconds to 30 seconds. The removal of the composition from the surface may be achieved by wiping the composition off the surface using a suitable wipe. Alternately it may be achieved by rising the surface with water to be substantially free of the composition. The composition is usually applied to the desired skin surface after diluting the composition with water. The composition may be diluted with water to a concentration of 1 to 50%, preferably 2 to 20% by weight of the diluted solution.

The invention will now be illustrated with reference to the following non-limiting examples.

EXAMPLES

Example A C, 1: Invitro Efficacy of Thymol with THPE

The following samples were tested for in-vitro antibacterial efficacy using the below mentioned protocol Example-A: Culture control
Example-B: 1% Tetra hydroxy propyl ethylene diamine (THPE)
Example-C: 0.01% Thymol
Example-1: 1% THPE+0.01% Thymol
Protocol:
Medium used:
Sodium phosphate buffer 10 mM for culture preparation pH 7.4
Organism
*E. coli* ATCC 10536
Procedure:

The test organism was subcultured from the glycerol stock (stored at −70° C.) onto a TSA slant and incubated at 37° C. for 18 to 24 hours. The slant was stored in a refrigerator for a maximum of two weeks after which a fresh slant was prepared.

The test organisms were streaked from TSA slants onto petri plates containing TSA and incubated at 37° C. for 21 to 22 hours before use.

The bacterial inoculums were prepared corresponding to $10^6$ cells in 10 mM Sodium Phosphate Buffer from the above plate.

The OD of culture was adjusted to 0.8 for *E. coli*, to give $10^8$ cells/ml. Once the bacterial inoculums corresponding to $10^8$ cells is prepared in sodium phosphate buffer, it is serially diluted to $10^6$ cells (1:10 dilution in 10 mM sodium phosphate buffer)

135 µl bacterial inoculums (from $10^6$ CFU/ml) was taken for all the treatments in a reaction volume of 300 µl (in a microtiter plate/96 well plate).

15 µl of 100 mM buffer was taken for all controls and treatments so that the final conc. corresponds to ~5 mM in all the reactions.

The respective compounds/actives to be tested were taken and made up to a volume of 300 µl with autoclaved distilled water.

Note: Each treatment is kept in duplicates.

The microtiter plate was incubated at 37° C. for a contact time of 4 hours and then plated on TSA after required serial dilutions in neutralizer D/E to study bacterial kill.

Plates were incubated overnight for *E. coli*

The colonies were counted to estimate the bacteria remaining and thereby the log kill.

The data on the average of bacteria remaining (in log cfu/ml) is summarised in Table-1.

TABLE 1

| Example | Sample | Average (log cfu/ml) | Std Dev |
|---|---|---|---|
| A | Culture control | 6.36 | 0.10 |
| B | 1% THPE | 5.98 | 0.11 |
| C | 0.01% Thymol | 6.26 | 0.16 |
| 1 | 1% THPE + 0.01% Thymol | 2.75 | 0.11 |

The data in Table-1 above indicates that the combination of thymol and THPE provides for synergistic antibacterial efficacy in comparison to the individual compounds.

Example D and 2: Invivo Antibacterial Efficacy of the Composition of the Invention in a Soap Base in Comparison to a Soap Composition without any Antibacterial Actives The following two soap bars were prepared as shown in Table-2 below

TABLE 2

| Ingredient (wt %) | Example D | Example 2 |
|---|---|---|
| Sodium laurate | 12.5 | 5.0 |
| Sodium Palmate | 66.5 | 54 |
| Glycerine | 2 | 4.0 |
| Sodium chloride | 0.7 | 0.7 |
| Sodium citrate | 0 | 1.8 |
| Fatty acid C12-18 | 0.25 | 9.5 |
| THPE | 0 | 2.0 |
| Thymol | 0 | 0.1 |
| Talc | 2.5 | 6.0 |
| Titanium dioxide | 0.5 | 0.5 |
| Minor ingredient, perfume & Water | upto 100 | upto 100 |

The above compositions were tested for invivo antibacterial activity using the below protocol:

1. A soap bar without any antimicrobial active was given to each volunteer to use for bathing, washing hands, washing forearms etc for 7 days wash off period before the trial began.
2. The volunteers were instructed to refrain from use of any leave on products (sun screen, hand sanitizer, skin moisturizers, lotion, cream, oil and antimicrobial products) till completion of the study.
3. Volunteers were asked to come to study site on day 8 without washing their forearm in the morning (preferably asked them to come to study site without taking bath)
4. On day 8, study person washed their one forearm with soap bar of Example D and other forearm with soap bar of Example-2.

5. The washing protocol was as follows.
   Temperature of tap water was 24° C.±2° C.
   Wet/dip the soap for 10 secs in the water.
   Wet each forearm with tap water (100 ml±10 ml).
   Apply the soap 10 times back and forth across the length of the forearm.
   Lather the forearm with gloved hand by taking 2 to 3 ml of water in the palm for 30 sec
   Lather retained on forearm for 20 secs
   Wash the forearm with running tap water to remove the soap completely for 1 min
   Remove excess water by patting dry using sterile tissue paper
   After 30 min of washing their forearm, 10 μl of *E. coli* (10536) from $10^8$ stock was applied on defined circular area on forearm skin (7 $cm^2$ circle) for 10 mins. ($10^8$ culture stock was prepared in 10 mM sodium phosphate buffer using 18 to 20 hrs old broth culture. The OD was adjusted to 0.8 at 620 nm to attain $10^8$ counts)
6. After 10 mins of contact time of *E. coli* on forearm skin, it was recovered by cup scrub method (ASTM method, E2752-10) using 1.5 ml of extraction buffer.
7. Then each sample was serially diluted in 9 ml of D/E (Dey Engley neutralizing broth) and respective dilutions were plated on MacConkey agar media.
8. Plates were incubated at 37° C. for 24 h to grow *E. coli* and then colonies were counted and the log cfu/ml was calculated by using standard microbiology method.
   Extraction Buffer
   Dissolved 0.4 gm KH2PO4, 10.1 g Na2HPO4, 1.0 g Triton X 100, 100.0 gm Tween 80 and 11.67 gm Lecithin in one liter purified hot water. Final pH was adjusted to 7.8±0.1. The buffer was vortexed immediately after autoclaving.

The data on the bacteria remaining after the above treatment is summarized in Table-3 below:

TABLE 3

| Example | Sample | Average (log cfu/ml) | Std Dev |
|---|---|---|---|
| D | Soap bar without antibacterial active | 4.1 | 0.15 |
| 2 | Soap bar with 2% THPE and 0.1% Thymol | 3.4 | 0.10 |

The data in Table-3 above indicates that a soap bar composition of the invention (Example-2) is able to provide antibacterial efficacy long after the skin surface has been washed with the composition which is much better as compared to a conventional soap bar (Example-D).

Example E-H and 3, 4: Invitro Efficacy of Carvacrol with THPE

Experiments similar to the ones carried out for thymol+THPE were carried out with carvacrol+THPE. The antibacterial efficacy was measured in vitro as detailed above for examples 1 and A-C. The antibacterial efficacy is summarized in Table-4 below:

TABLE 4

| Example | Sample | Average (log cfu/ml) | Std Dev |
|---|---|---|---|
| E | Culture control | 6.41 | 0.22 |
| F | 0.01% carvacrol | 6.12 | 0.17 |

TABLE 4-continued

| Example | Sample | Average (log cfu/ml) | Std Dev |
|---|---|---|---|
| G | 0.5% THPE | 5.97 | 0.31 |
| H | 1% THPE | 5.45 | 0.31 |
| 3 | 0.5% THPE + 0.01% carvacrol | 2.01 | 0.29 |
| 4 | 1% THPE + 0.01% carvacrol | 1.00 | 0.10 |

The data in the table-4 above indicates that similar synergistic activity is obtained for a combination of carvacrol with THPE as compared to thymol+THPE.

Example I-K and 5: Invitro Efficacy of Eugenol with THPE

Experiments similar to the ones carried out for thymol+THPE were carried out with eugenol+THPE. The antibacterial efficacy was measured in vitro as detailed above for examples 1 and A-C. The antibacterial efficacy is summarized in Table-5 below:

TABLE 5

| Example | Sample | Average (log cfu/ml) | Std Dev |
|---|---|---|---|
| I | Culture control | 6.23 | 0.03 |
| J | 0.01% Eugenol | 6.15 | 0.17 |
| K | 1% THPE | 5.44 | 0.29 |
| 5 | 1% THPE + 0.01% Eugenol | 4.61 | 0.40 |

The data in the table-5 above indicates synergistic activity for a combination of eugenol with THPE although the effect is not as significant as for thymol+THPE

The invention claimed is:
1. An antimicrobial composition comprising:
   (i) 0.1 to 10 wt % of a compound of general formula 1

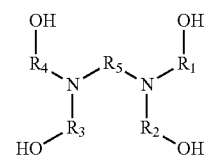

where R1 to R4 are each independently a linear or branched carbon chain having 2 to 5 carbon atoms; and R5 is a carbon chain having 1 to 4 carbon atoms, wherein the compound of formula one is tetrahydroxypropyl ethylenediamine having the formula

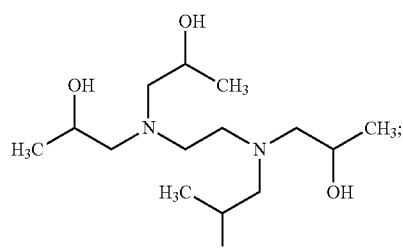

and
(ii) 0.001 to 1 wt % of an essential oil compound of general formula 2 having the structure

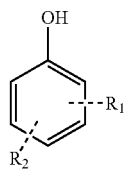

where R1 is H, OH or OR where R is an alkyl chain with 1 to 5 carbon atoms;
R2 is a C1 to C6 linear alkyl group; or C3 to C6 branched alkyl group; or C5 to C6 cyclic or heterocyclic alkyl group; or a C6 aromatic group;
wherein said essential oil compound is selected from thymol, carvacrol, 2-propyl phenol, 4-pentyl phenol, 4-sec-butylphenol, 2-benzyl phenol, eugenol or combinations thereof;
wherein the composition is used for skin cleansing.

2. The antimicrobial composition as claimed in claim 1, wherein the essential oil compound is thymol, carvacrol or eugenol.

3. The antimicrobial composition as claimed in claim 1, wherein the composition additionally comprises terpineol.

4. The antimicrobial composition as claimed in claim 3, comprising a mixture of terpineol and the essential oil compound thymol.

5. The antimicrobial composition as claimed in claim 1, additionally comprising a cosmetically acceptable base.

6. The composition as claimed in claim 5, wherein said cosmetically acceptable base comprises water, surfactant or combinations thereof.

7. The composition as claimed in claim 6, wherein said surfactant is an anionic surfactant.

8. A method of providing antimicrobial efficacy to skin comprising the step of applying a composition as claimed in claim 1 on to a desired skin surface, followed by wiping the composition off the surface or rinsing the surface with water to be substantially free of said composition.

9. The antibacterial composition as claimed in claim 7, wherein the anionic surfactant is soap.

10. The method as claimed in claim 8, wherein said composition is applied to the desired skin surface after diluting the composition with water.

11. The method as claimed in claim 10, wherein the composition is diluted with water to a concentration of 1 to 50%.

12. The method as claimed in claim 8, wherein the step of wiping or rinsing is carried out 10 seconds to 2 minutes after applying the composition.

13. The method as claimed in claim 10, wherein the composition is 2 to 20% by weight of the diluted solution.

* * * * *